US005605158A

United States Patent [19]
Snell

[11] Patent Number: 5,605,158
[45] Date of Patent: Feb. 25, 1997

[54] APPARATUS FOR ANNOTATING PHYSIOLOGICAL WAVEFORMS

[75] Inventor: Jeffery D. Snell, Oak Park, Calif.

[73] Assignee: Pacesetter, Inc., Sylmar, Calif.

[21] Appl. No.: 510,448

[22] Filed: Aug. 2, 1995

[51] Int. Cl.⁶ ............................. A61B 5/04; A61B 5/0402; A61B 5/044
[52] U.S. Cl. ..................... 128/696; 128/710; 128/712
[58] Field of Search .................... 128/696, 710, 128/712

[56] References Cited

U.S. PATENT DOCUMENTS

| | | | |
|---|---|---|---|
| 3,782,367 | 1/1974 | Hochberg et al. | 128/697 |
| 4,098,267 | 7/1978 | Stein et al. | 128/712 |
| 4,281,664 | 8/1981 | Duggan | 128/696 |
| 4,374,382 | 2/1983 | Markowitz | 128/696 |
| 4,527,567 | 7/1985 | Fischler et al. | 128/697 |
| 4,596,255 | 6/1986 | Snell et al. | 128/697 |
| 4,601,291 | 7/1986 | Boute et al. | 128/710 |
| 4,791,936 | 12/1988 | Snell et al. | 128/697 |
| 4,809,697 | 3/1989 | Causey, III et al. | 607/31 |
| 4,825,869 | 5/1989 | Sasmor et al. | 607/27 |
| 5,113,869 | 5/1992 | Nappholz et al. | 128/696 |
| 5,224,486 | 7/1993 | Lerman et al. | 128/696 |
| 5,447,164 | 9/1995 | Shaya et al. | 128/710 |
| 5,469,858 | 11/1995 | Osborne | 128/710 |

*Primary Examiner*—William E. Kamm
*Assistant Examiner*—Carl H. Layno
*Attorney, Agent, or Firm*—Harold C. Schloss

[57] ABSTRACT

An apparatus for annotating physiological waveforms is provided. The apparatus comprises an implantable medical device, which may be a pacemaker or a cardioverter/defibrillator, and a programmer for use with the implantable medical device. The implantable medical device may be modeled as a finite state machine. Whenever the implantable medical device enters a new state, a state transition vector or a current state vector is transmitted to the programmer. The programmer implements a state machine model of the implantable medical device to determine the current state of the device based on the received state vectors. Because the exact state of the implantable medical device is known, the programmer can annotate the physiological waveform more completely than has previously been possible. For example, when the behavior of the implantable medical device is unclear, the programmer can place an explanatory label adjacent to the displayed physiological waveform.

83 Claims, 2 Drawing Sheets

APPARATUS FOR ANNOTATING PHYSIOLOGICAL WAVEFORMS

BACKGROUND OF THE INVENTION

The present invention relates to displaying waveforms retrieved from implantable medical devices. More particularly, this invention relates to storing and annotating portions of such a waveform.

Implantable medical devices are becoming increasingly more complex. As these devices become more complex they perform more functions. These devices frequently measure some physiologic parameter such as a patient's intracardiac electrogram, blood oxygen level, activity level, respiration rate, or body temperature. These devices may also analyze the measured parameter. Some devices provide some response as a result of that analysis. Often, the analysis may have multiple levels of detail associated with it. There may be a simplistic instantaneous diagnosis of the patient's condition, as well as a longer term, more sophisticated analysis. For example, a cardiac monitoring device may detect a series of contractions in the patient's right atrium. A more sophisticated analysis of this same signal would include rate information, and the detection of a possible atrial tachycardia or atrial fibrillation if the rate of the detected atrial contractions exceeds a preset rate for some preset length of time. Other implantable medical devices that could utilize similar diagnostic capabilities include, muscle stimulators, drug pumps, nerve stimulators, artificial organs and/or cardiac stimulating devices.

Cardiac stimulating devices such as pacemakers and cardioverter/defibrillators measure the patient's intracardiac electrogram or electrocardiogram. Newer devices may also have the capability to react to various physiologic parameters such as a patient's activity level or blood oxygen level. Cardiac stimulating devices may also be capable of terminating potentially dangerous cardiac arrhythmias. To perform these tasks, cardiac stimulating devices contain microprocessors and control circuitry that allow the devices to respond to a patient's heartbeat and other measured parameters. The patient's internal heartbeat signals, which are known as the intracardiac electrogram, are measured through leads attached to the patient's heart.

A cardiac stimulating device can respond to different cardiac conditions with varying levels of therapy. For example, some cardiac stimulating devices have the capability to treat heart arrhythmias such as tachycardia. Such devices confirm the onset of tachycardia when a set of detection criteria has been satisfied. Once a tachycardia episode is confirmed, increasing levels of therapy can be applied to the patient's heart to attempt to terminate the episode.

Many cardiac stimulating devices have adjustable settings, which a physician can select and enter into the device using a "programmer." Although default settings for the detection criteria and corresponding levels of therapy can be used, it is usually beneficial if the physician programs each individual patient's cardiac stimulating device, so that the specific characteristics of the patient's heart can be taken into account. Without tailoring the device settings, some patients may experience discomfort if they suffer from a cardiac condition that is not detected and treated adequately or sufficiently early by the cardiac stimulating device.

In order to properly adjust the settings of a cardiac stimulating device, physicians often analyze a patient's electrocardiogram (EKG). Physicians also analyze a patient's intracardiac electrogram, because the intracardiac electrogram is the signal that the cardiac stimulating device actually monitors during operation. The cardiac simulating device transmits the intracardiac electrogram to the programmer in real-time using radio-frequency telemetry. Either the intracardiac electrogram or the EKG may be displayed on a monitor or a chart recorder, for the physician's review.

During the course of monitoring the patient's heart, the cardiac stimulating device must identify which portions of the intracardiac electrogram represent certain cardiac events, such as the occurrence of a P-wave or an R-wave. Event markers, such as the letter "P" representing a measured P-wave, are generated whenever a cardiac event is detected by the cardiac stimulating device. Additional markers corresponding to events such as the application of a pacing pulse to the ventricle of the patient's heart are also generated. These markers are also transmitted to the programmer.

As described in Snell et al. U.S. Pat. Nos. 4,596,225 and 4,791,936, when displaying the intracardiac electrogram, it is a useful aid to display the event markers on the monitor or chart recorder adjacent to the event that each marker represents. For example, as shown in the aforementioned Snell et al. patents, the letter "P" can be placed on the display above the portion of the intracardiac electrogram that represents a P-wave. The letter "A" can be placed on the display above the portion of the intracardiac electrogram that represents application of a pulse to the atrium. Other events, such as the occurrence of an R-wave, or the application of a pulse to the ventricle can also be labeled "R" and "V", respectively. When the intracardiac electrogram is labeled with the event markers, the physician can more easily determine if the cardiac stimulating device is operating properly.

However, the response of the cardiac stimulating device to the measured intracardiac electrogram may be quite complex. In many cases, the physician may not be able to quickly determine if a device is responding correctly, because the cause of the device's behavior is not readily apparent. For example, it may be unclear when a tachycardia episode has been confirmed or what level of therapy is being applied to a patient's heart. Another example of a situation in which the behavior of the cardiac stimulating is unclear occurs when the cardiac stimulating device drops a pulse in order to terminate an episode of pacemaker mediated tachycardia ("PMT"). A PMT episode may occur when a pulse that is applied to a patient's ventricle is fed back to the patient's atrium via a retrograde conduction path in the heart. If the cardiac stimulating device is tracking the patient's atrial heart rate, the pulse that is fed back may be mistaken for the patient's normal sinus rhythm, which causes the cardiac stimulating device to apply increasingly fast pacing pulses to the patient's ventricle, until the maximum allowed pacing rate is reached. A pulse can be dropped to attempt to break this potentially harmful condition after a number of pulses have been applied at the maximum rate. However, unless the physician is aware that this is the reason for the missing pulse, it may appear that the device is not functioning properly.

The physician may not immediately know whether it is appropriate for a cardiac stimulating device to drop a pulse because the device makes this determination over a period of many heartbeats. For example, the cardiac stimulating device can be programmed to drop a pulse if more than 127 pulses are applied at the maximum rate. The device is allowed to apply a relatively large number of pulses to the heart at the maximum rate, because it may cause discomfort to the patient to drop pulses more frequently. However, it may be impractical for the physician to review the rate at which the last 127 pulses were applied. This information might no longer appear on the display, or even if the pulses were recorded in memory or on a strip chart, manual review might be unduly burdensome. Additionally, the behavior of each cardiac stimulating device differs, which further impedes the physician's efforts to evaluate device performance. Devices from different manufacturers are often incompatible and the operational characteristics of many cardiac stimulating devices depend on the selected values of the programmable parameters.

It would therefore be desirable to annotate the intracardiac electrogram or electrocardiogram to more completely reflect the state of the cardiac stimulating device. For example, when the cardiac stimulating device drops a pulse to terminate a PMT episode, the cardiac waveform adjacent to the missing pulse could be labeled "attempted PMT termination." When a cardiac stimulating device applies pulses to the heart in response to the confirmation of an episode of tachycardia, the annotation "tachycardia confirmed" could appear.

Alternatively, it may be desirable to annotate the intracardiac electrogram or electrocardiogram to more completely reflect the state of a cardiac monitoring device. In another alternative, any implantable medical device that monitors a measured value may have additional annotations displayed when accumulated individual measurements trigger detection of a more complex state by an implantable medical device.

SUMMARY OF THE INVENTION

These and other objects of the invention are accomplished in accordance with the principles of the present invention by providing an apparatus for annotating cardiac waveforms. In addition to labeling the waveforms with the traditional event markers, such as those designating P-waves, R-waves, and ventricular pacing pulses, the cardiac waveform may be labeled whenever the cardiac stimulating device performs a function of potential interest to the physician. To avoid cluttering the display, some functions are not labeled. However, when the physician desires to analyze a portion of the signal in more detail, a more complete annotation can be made.

Further, the physician can select between different levels of annotation. If desired, only the traditional event markers can be displayed. The event markers can also be supplemented by generating labels whenever the cardiac stimulating device implements a significant device function. The displayed cardiac waveform may also be fully annotated to reflect each change in the state of the cardiac stimulating device. In order to track the state of the cardiac stimulating device, vectors corresponding to the device's current state and changes in the device's state are telemetered to the programmer, which determines the current state of the device. The programmer then annotates the cardiac waveform accordingly.

An apparatus for annotating cardiac waveforms is therefore provided that has a cardiac stimulating device and a programmer. The cardiac stimulating device contains a sensing circuit for measuring a patient's heartbeat signals. The cardiac stimulating device also contains a controller that creates either state transition vectors, current state vectors, or both. These vectors describe the various states of the cardiac stimulating device. Also contained within the device is a communications unit for transmitting signals from the cardiac stimulating device. The programmer receives the transmitted signals using a telemetry head. The programmer may receive a cardiac waveform either from the cardiac stimulating device or from another source such as a surface electrocardiogram machine. Regardless of its source, the cardiac waveform is stored in a memory array by a control unit. The control unit also models the cardiac stimulating device's operation as a finite state machine. By modeling the device in this way, the control unit generates a series of current state signals that are stored in the memory array with the cardiac waveform. The control unit generates annotating labels that describe the operation of the cardiac stimulating device based on the values of the current state signals. Both the cardiac waveform and the annotating labels are displayed on a monitor.

Further in accordance with the invention a cardiac stimulating device programmer is provided that has a telemetry head for receiving signals from a cardiac stimulating device. The cardiac stimulating device transmits state transition vectors, or current state vectors, or both. The programmer also receives a patient's cardiac waveform and stores it in a memory array. A control unit within the programmer implements a state machine model of the cardiac stimulating device to calculate the values of current state signals. This calculation is based on the values of the received state transition vectors and/or received current state vectors. The programmer further has a monitor on which the cardiac waveform that is stored in the memory is displayed. The control unit generates annotating labels that correspond to each transition in the state of the cardiac stimulating device in terms that are relevant to the medical professional that is using the system. The control unit performs this function based on the values of the current state signals that are stored in the memory array. The control unit displays at least some of the annotating labels on the monitor adjacent to the displayed cardiac waveform.

Also in accordance with the present invention, a method of annotating a cardiac waveform with labels is provided. The method involves receiving a patient's cardiac waveform and receiving signals from a cardiac device. The signals that are received from the cardiac device include state transition vectors, or current state vectors, or both. The state transition vectors represent each transition in the state of the cardiac device, whereas the current state vectors represent the current state of the device. The method also involves the step of storing the cardiac waveform in a memory array. A state machine model of the cardiac stimulating device is also implemented, which allows the current state of the cardiac device to be determined from the values of the state transition vectors or the current state vectors. Current state signals are stored in the memory array. The method further involves displaying the cardiac waveform on a monitor. Annotating labels corresponding to each transition in the state of the cardiac device are also generated based on the values of the current state signals that are stored in the memory. The annotating labels are displayed on the monitor adjacent to the displayed cardiac waveform.

An alternate embodiment is an external monitoring system for a implantable cardiac monitoring device. The cardiac monitoring device transmits state transition vectors, or current state vectors, or both. The external monitoring system may also receive a patient's cardiac waveform, and store it in a memory array. A control unit within the external monitoring system implements a state machine model of the cardiac monitoring device to calculate the values of the current state signals. This calculation is based on the values of the received state transition vectors and/or the received current state vectors. The external monitoring system further has a monitor on which the cardiac waveform that is stored in the memory is displayed (if the cardiac waveform is sent).

The control unit generates annotating labels that correspond to each transition in the state of the cardiac monitoring device in terms that are relevant to the medical professional using the system. The control unit performs this function based on the values of the current state signals that are stored in the memory array. The control unit displays at least some of the annotating labels on the monitor. If the cardiac waveform is sent by the implantable cardiac monitoring device, or if another cardiac waveform is received, these labels are displayed adjacent to the displayed cardiac waveform.

Other alternatives may include any implantable medical device that measures a parameter. Such a device may transmit the measured signal, and state transition vectors and/or current state vectors. An external monitoring apparatus can be used to display the measured signal and annotations that describe the associated state of the implanted medical device.

BRIEF DESCRIPTION OF THE DRAWINGS

The above and other advantages of the invention will be apparent upon consideration of the following detailed description, taken in conjunction with the accompanying drawings, in which like reference numerals refer to like parts throughout, and in which.

DETAILED DESCRIPTION OF THE PREFERRED EMBODIMENTS

Figure 1:
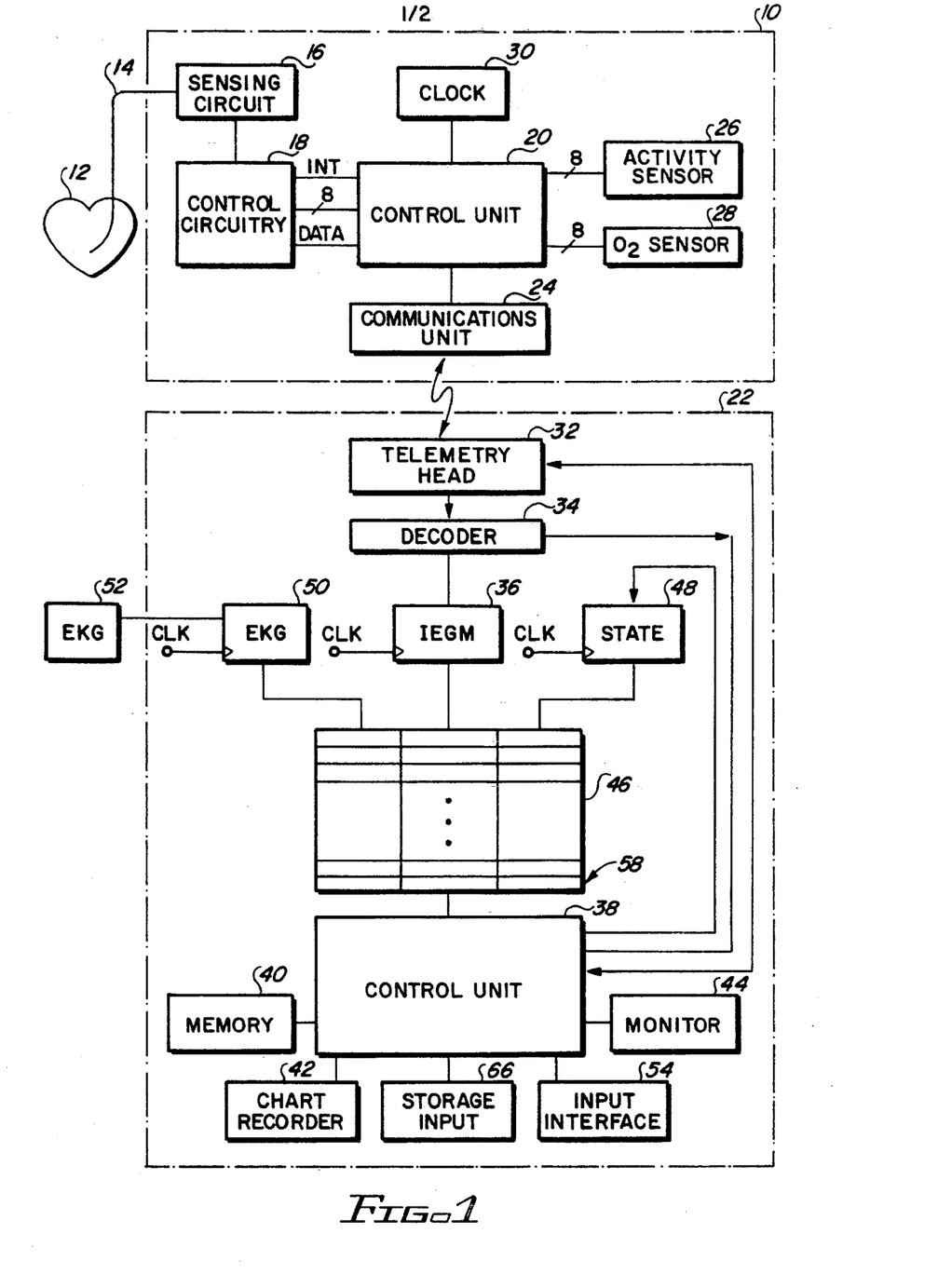
FIG. 1 is a schematic diagram showing an apparatus for annotating cardiac waveforms in accordance with the present invention.

An apparatus constructed in accordance with the present invention is shown in FIG. 1. A cardiac stimulating device 10 is connected to a patient's heart 12 via a lead 14. The patient's intracardiac electrogram (IEGM) is measured by a sensing circuit 16, which passes the IEGM to control circuitry 18. The control circuitry 18 analyzes the intracardiac electrogram to determine when cardiac events occur. When a cardiac event is sensed, the control circuitry changes the state of one of the bits in an eight-bit register (not shown) contained within the control circuitry 18. For example, if a P-wave is sensed by the control circuitry 18, a logical one is stored in the bit in the eight-bit register that corresponds to detected P-waves. Similarly, if an R-wave is sensed or if the ventricle is paced, a logical one can be stored in either the bit corresponding to detected R-waves or the bit corresponding to ventricle pacing. In each case, when one of the bits of the eight-bit register becomes a logical one, the remaining bits become logical zeros. After the eight-bit register is updated to reflect the most recent detected event, the control circuitry generates an interrupt, which is transmitted to a control unit 20. When the control unit 20 receives the interrupt, the data in the eight-bit register is transferred to the control unit 20 from the control circuitry 18. The control circuitry 18 also provides the digitized intracardiac electrogram to the control unit 20, so that it may be telemetered in real-time to a programmer 22 via a communications unit 24. The control unit 20, which is preferably microprocessor based, also monitors sensors such as an activity sensor 26 and an oxygen sensor 28, as well as a real-time clock 30. Typically, the control unit reads data from the sensors after receiving confirmation of the detection of an R-wave or a ventricular pulse.

When a physician desires to display a patient's IEGM, the cardiac stimulating device telemeters the IEGM to the programmer 22 via the communications unit 24. Regardless of whether the physician elects to display the IEGM or the EKG, the programmer 22 receives the data necessary to annotate the cardiac waveform from the cardiac stimulating device 10. As described above, this data has previously consisted of event markers representing the cardiac events that have traditionally been sensed by cardiac stimulating devices, such as the occurrence of P-waves and R-waves. However, in order to more fully annotate the EKG or the IEGM, additional data is required. Although the behavior of the cardiac stimulating device 10 may be complex, the device may still be modeled as a finite state machine. Because each of the device's states may potentially be of interest to the physician, the cardiac stimulating device preferably telemeters a state transition vector to the programmer 22 each time the device changes its state.

A state transition vector is shorter than the current state vector that represents the actual state of the cardiac stimulating device, because the state transition vector only identifies the change between a new state and the previous state. Occasionally, however, the current state vector may be transmitted to the programmer 22, so that the state of the device may not be lost due to a single garbled transmission. The current state vector can be sent once each heartbeat, following an R-wave or a ventricular pacing pulse. Alternatively, the current state vector can be sent at fixed intervals. Another alternative is to send only the current state vector, thereby ensuring that the programmer always knows the current state of the device. Finally, the vectors may also identify concurrently detected events that do not cause a change in the state of the device. For example, during the refractory period following a ventricular output pulse a cardiac stimulating device may detect, yet otherwise ignore, R-waves.

Signals that are transmitted by the cardiac stimulating device 10 are received by the programmer 22 via a telemetry head 32. The signals contain tags that allow a decoder 34 to determine whether the signals correspond to IEGM data or state vectors. Signals corresponding to IEGM data are directed to queue logic 36, whereas state vectors are directed to a control unit 38. The state machine model of the cardiac stimulating device 10 is implemented by the control unit 38, so that upon receiving a state transition vector, the control unit 38 can determine the current state of the cardiac stimulating device 10 and generate a corresponding current state signal. This signal is subsequently stored in a portion of a memory 40. If a current state vector is received, it may be compared with the value of the current state that is stored in the memory 40 to determine whether an error has occurred in tracking the state of the cardiac stimulating device. If the states differ, the stored state may be replaced with the received current state vector.

Annotated cardiac waveforms may be displayed on a chart recorder 42 or a monitor 44. The IEGM data from the queue logic 36 and the current state signals corresponding to the current state of the cardiac stimulating device 10 are directed to a memory array 46, which may be implemented using a shift register or random access memory organized as a circular buffer. The current state signals pass through a clocked buffer 48 to overcome timing skew. The queue logic 36 is also clocked, as is an EKG input device 50, which is used to receive EKG signals from an optional EKG system 52. Because the control unit 38 may take several clock cycles to generate a current state signal, the current state signals will typically lag behind the EKG data and the IEGM data. By delaying the EKG data with the EKG input device, the EKG data may be synchronized with the current state signals. Similarly, the queue logic 36 may delay the IEGM data. While displaying the annotated cardiac data on the monitor 44, a user interacts with the programmer 22 via input interface 54, which may be, for example, a keyboard, a mouse, or a touch screen.

Figure 2:
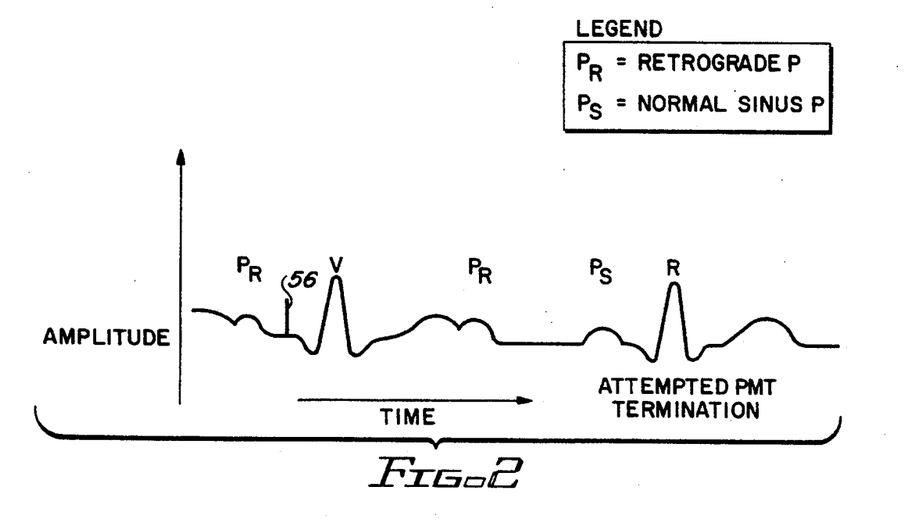
FIG. 2 shows a representative annotated cardiac waveform as it appears on a monitor.

A cardiac waveform that has been annotated in accordance with the present invention is shown in FIG. 2. P-waves are labeled with the letter "P", while ventricular pacing is represented by the letter "V". A sensed R-wave is denoted with the letter "R". FIG. 2 also illustrates how the cardiac waveform may be annotated in more detail to reflect the behavior of the cardiac stimulating device, for example, when the device is attempting to terminate a PMT episode. As described above, if a pacing pulse 56 is applied to the patient's heart at the maximum pacing rate for 127 pulses, the cardiac stimulating device 10 (FIG. 1) may drop the next pulse in an attempt to break what appears to be a PMT episode. In this event, the programmer 22 (FIG. 1) will place the label "attempted PMT termination" adjacent to the location of the missing pulse. Similar labels may be generated for each of the states of the cardiac stimulating device. For example, when the device confirms an episode of tachycardia, the waveform may be annotated with the label "tachycardia confirmed". Similarly, whenever the device applies a therapy to the patient's heart, a label describing the therapy can be displayed.

Referring again to FIG. 1, during the annotation of the cardiac waveform, the control unit 38 retrieves the desired IEGM or EKG data and the state of the cardiac stimulating device 10 from the memory array 46. Only the portion of the cardiac waveform that is to be displayed is retrieved, although the remainder of the signal and the corresponding state signals are retained in the memory array 46 for later review by the physician. If the physician directs the programmer to display every state transition of the cardiac stimulating device 10, then each state that is recorded in the memory array 46, will be converted into a label by the control unit 38 and subsequently displayed on the monitor 44. Because the state signals in the memory array 46 are synchronized with the IEGM and EKG data, the control unit 38 may display the data and the state of the device synchronously by retrieving the data and state signals from the same row 58 of the memory array 46.

The physician may also direct the programmer 22 to display only the traditional event markers, such as those denoting P-waves and R-waves. In this mode of operation, the control unit 38 would not generate labels such as the label "attempted PMT termination". Alternatively, the user may direct the programmer 22 to display only those labels deemed to be of significant interest. For example, the label "attempted PMT termination" could be displayed, whereas no label would be generated to denote when the cardiac stimulating device is merely in the state of counting the number of pacing pulses required to trigger the "attempted PMT termination" label.

Figure 3:
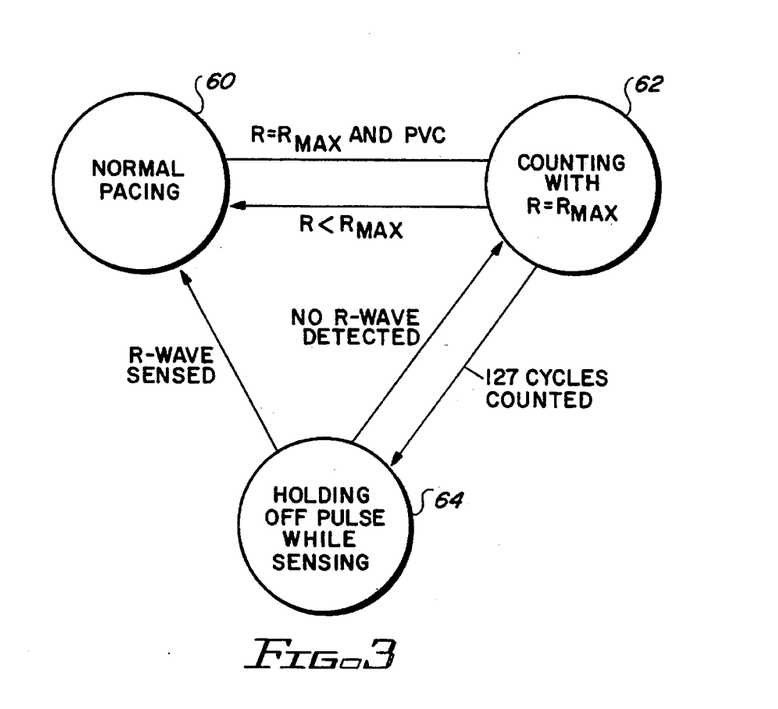
FIG. 3 is a schematic diagram showing a state machine representation of the operation of a cardiac stimulating device.

The present invention may be further understood by referring to FIG. 3, which illustrates a typical example of the state machine approach to characterizing the behavior of the cardiac stimulating device 10. The state machine diagram shows a method of detecting and attempting to terminate PMT episodes similar to the method described above. In contrast to the previously described method of terminating PMT episodes, with this method a further condition—the detection of a premature ventricular contraction (PVC)—is required before the cardiac stimulating device counts the number of pacing pulses that are applied at the maximum pacing rate.

In a normal pacing state 60 the cardiac stimulating device 10 applies pacing pulses to the patient's heart at the rate, R, as needed. Premature ventricular contractions, which are defined as the occurrence of an R-wave without an immediately preceding P-wave, have been found to initiate a pacemaker mediated tachycardia. In order to reduce the frequency with which pacing pulses are dropped, the cardiac stimulating device 10 will not enter a counting state 62 unless a PVC has been detected and the heart rate equals the maximum allowed pacing rate, RMAX. If the heart rate drops below the maximum rate, the cardiac stimulating device 10 returns to the normal pacing state 60. If, however, 127 heartbeat cycles are counted in the counting state 62, the cardiac stimulating device 10 enters an inhibiting state 64, in which no pacing pulses are applied to the heart for a predetermined period of time while the heart is monitored to determine if an R-wave occurs. If no R-wave is detected, the cardiac stimulating device 10 returns to the counting state 62, whereas if an R-wave is detected, the device enters the normal pacing state 60.

In order for the programmer 22 to model the operation of the cardiac stimulating device 10 as a state machine, each state transition, such as the transitions shown in FIG. 3, must be taken into account. The state machine model for each type of cardiac stimulating device to be supported by the programmer 22 is stored in a storage unit 66 by the control unit 38 (FIG. 1). If the programmer 22 is used with a cardiac stimulating device that only generates traditional event markers, the decoder 34 will direct the traditional markers to the control unit 38, which will store these markers in the memory array 46 in place of the current state signals.

The programmer 22 allows the user to freeze the display and subsequently review the saved cardiac data and the saved states of the cardiac stimulating device. If 16 kilobytes of memory are dedicated to data storage, then at a sampling rate of 400 hertz, approximately 40 seconds of cardiac signals can be stored. Using the input interface 54, a user can select portions of the signal to analyze more completely. For example, if a physician observes that the cardiac stimulating device 10 has dropped a pacing pulse, the physician may highlight the area of interest on the display. The control unit 38 then retrieves the corresponding current state from the memory array 46, so that the cardiac waveform can be fully annotated. If the cardiac waveform had previously only been labeled with event markers, the control unit 38 may generate more detailed labels. Further, the control unit 38 may provide an even more complete explanation of the state of the cardiac stimulating device 10, if desired, by displaying supplemental text on a separate region of the monitor.

In another alternative embodiment, the implanted device may be a cardiac monitor. The cardiac monitor would detect tachycardia, with the programmer displaying these tachycardia detections at the direction of the physician as described earlier. One skilled in the art will appreciate that the present invention can be practiced by other than the described embodiments, which are presented for purposes of illustration and not of limitation, and the present invention is limited only by the claims that follow.

What is claimed is:

1. An apparatus for monitoring a parameter indicative of a patient's condition, comprising an implantable medical device having a plurality of operating states and an external monitoring device, wherein the implantable medical device comprises:

means for detecting at least one physiological parameter of the patient and for producing a characteristic signal in response thereto;

control means for comparing the characteristic signal to preset criteria for detecting the occurrence of a physiological event and for changing the operating state of said implantable medical device in response thereto;

means for transmitting event codes representative of the state of the implantable medical device; and means for transmitting event codes representative of the occurrence of a physiological event;

and wherein said monitoring device comprises:

means for receiving said transmitted event codes;

means for selectively displaying annotating labels, at least some of said annotating labels functioning to represent one or more of said received event codes;

means for selectively determining annotating labels to be displayed; and means for receiving a user input, wherein said user input selects a subset of annotating labels to be displayed.

2. An apparatus, as defined in claim 1, wherein said means for detecting a physiological parameter comprises means for detecting a cardiac waveform.

3. An apparatus, as defined in claim 2, wherein said implantable medical device further comprises means for electrically stimulating the patient's heart.

4. An apparatus, as defined in claim 2, wherein said implantable medical device further comprises:

means for transmitting said detected cardiac waveform;

and wherein said monitoring device further comprises:

means for receiving said transmitted cardiac waveform; and means for displaying said received cardiac waveform concurrently with said annotating labels as said cardiac waveform is received.

5. An apparatus, as defined in claim 4, further comprising:

an input interface for directing said monitoring device to freeze a display for review thereon, whereby said input interface further comprises:

means for highlighting a portion of the displayed cardiac waveform, and means for directing said monitoring device to display additional annotating labels to further explain the operation of said implantable medical device in the vicinity of said highlighted portion of said displayed cardiac waveform.

6. An apparatus, as defined in claim 2, wherein said monitoring unit displays said annotating labels at one of three selected levels comprising:

(a) a first level in which only annotating labels which comprise traditional event markers are displayed;

(b) a second level in which said traditional event markers are supplemented with additional annotating labels; and (c) a third level in which an annotating label corresponding to each transition in the operating state of said implantable medical device is displayed on said monitor.

7. An apparatus, as defined in claim 4, wherein said monitoring device further comprises:

means for receiving an electrocardiogram generated by an electrocardiogram measurement system; and means for displaying said received electrocardiogram concurrently with said received cardiac waveform and said annotating labels as said electrocardiogram is received.

8. An apparatus, as defined in claim 7, wherein said monitoring device further comprises:

a memory array; and means for synchronizing said received electrocardiogram, said received cardiac waveform, and said received event codes in said memory array.

9. An apparatus, as defined in claim 2, wherein said means for detecting said cardiac waveform comprises means for detecting the intracardiac electrogram, and wherein said implantable medical device transmits the patient's intracardiac electrogram to said monitoring device.

10. An apparatus, as defined in claim 1, wherein said means for transmitting event codes representative of the state of the implantable medical device comprises means for transmitting current state vectors, said current state vectors representing the current state of said implanted medical device.

11. An apparatus, as defined in claim 1, wherein said monitoring device further comprises means for simulating the implantable medical device as a state machine using said received event codes and for generating current state signals that are representative of the current state of said implantable medical device.

12. An apparatus, as defined in claim 1, wherein said means for transmitting event codes representative of the state of the implantable medical device comprises means for transmitting state transition vectors, each state transition vector representing the change in state of said implantable medical device from the previous state transition vector.

13. An apparatus, as defined in claim 12, wherein said means for transmitting event codes representative of the state of the implantable medical device further comprises means for periodically transmitting current state vectors, said current state vectors representing the current state of said implanted medical device.

14. A programmer for use with an implantable medical device having means for transmitting vectors representative of the state of the implantable medical device, the programmer comprising:

receiver means for receiving the transmitted vectors;

memory means having a plurality of memory locations;

control means for:

(a) generating a current state signal from the received vectors, such current state signal representative of the current state of the implantable medical device;

(b) storing said current state signal in a first memory location; and (c) generating annotating labels corresponding to said current state signal;

means for displaying a selected subset of the annotating labels; and an input interface, operably connected to said control means, for selecting the subset of annotating labels to be displayed.

15. A programmer, as defined in claim 14, wherein said control means continuously updates the displayed annotating labels such that only the most recent annotating labels are displayed.

16. A programmer, as defined in claim 15, further comprising:

an input interface operably connected to said control means, said input interface being operable to direct said control means to freeze the displayed annotating labels for review by halting the update of said displayed annotating labels, said input interface also being operable to direct said control unit to identify a portion of the displayed annotating labels, wherein said control means comprises means for displaying an alternate set of annotating labels, further wherein said input interface being operable to direct said control means to display said alternate set of annotating labels relating to such identified portion of annotating labels.

17. A programmer, as defined in claim 16, wherein said means for displaying an alternate set comprises means for displaying a superset of the prior displayed annotating labels.

18. A programmer, as defined in claim 16, wherein said means for displaying an alternate set comprises means for displaying a subset of the prior displayed annotating labels.

19. A programmer as defined in claim 14, wherein said vectors are state transition vectors representing changes in the state of the implantable medical device, and wherein said control means for generating a current state signal comprises means for generating a current state signal from state transition vectors.

20. A programmer as defined in claim 14, wherein said vectors are current state vectors representing the current state of the implantable medical device, and wherein said control means for generating a current state signal comprises means for generating a current state signal from current state vectors.

21. The programmer as defined in claim 14, wherein said vectors are current state vectors representing the current state of the implantable medical device and state transition vectors representing changes in the state of the implantable medical device, and wherein said control means for generating a current state signal comprises means for generating a current state signal from current state vectors and state transition vectors.

22. A programmer as defined in claim 14, wherein said vectors are also representative of concurrently detected events, wherein said control means further comprises:

means for generating a detected event signal from the received vectors;

means for storing said detected event signal; and means for generating annotating labels corresponding to said detected event signal.

23. A programmer as defined in claim 14, wherein said implantable medical device also has means for detecting a physiological parameter and means for transmitting a physiological signal representative of the physiological parameter, further comprising:

means for receiving the physiological signal;

means for displaying said physiological signal; and wherein said control means further comprises means for storing said physiological signal in a second memory location.

24. A programmer as defined in claim 14, further comprising:

means for detecting a first physiological parameter;

means for generating a first physiological signal from said detected first physiological parameter;

means for displaying said first physiological signal; and wherein said control means further comprises means for storing said first physiological signal in a second memory location.

25. A programmer as defined in claim 24, wherein said control means continuously updates the displayed annotating labels and displayed first physiological signal such that only the most recent annotating labels and the most recent first physiological signal are displayed.

26. A programmer as defined in claim 25, further comprising:

an input interface operably connected to said control means, said input interface being operable to direct said control means to freeze the displayed annotating labels and displayed first physiological signal for review by halting the update of said displayed annotating labels and said displayed first physiological signal, said input interface also being operable to direct said control unit to identify a portion of the displayed annotating labels and a corresponding portion of said displayed first physiological signal, said input interface being operable to direct said control means to display an alternate set of annotating labels relating to such identified portion of annotating labels.

27. A programmer as defined in claim 22, wherein said implantable medical device also has means for detecting a second physiological parameter and means for transmitting a second physiological signal representative of the second physiological parameter, further comprising:

means for receiving the second physiological signal;

means for displaying said second physiological signal; and wherein said control means further comprises means for storing said second physiological signal in a third memory location.

28. A programmer as defined in claim 27, wherein said control means continuously updates the displayed annotating labels, displayed first physiological signal, and displayed second physiological signal such that only the most recent annotating labels and the most recent physiological signals are displayed.

29. A programmer as defined in claim 28, further comprising:

an input interface operably connected to said control means, said input interface being operable to direct said control means to freeze the displayed annotating labels and displayed physiological signals for review by halting the update of said displayed annotating labels and said displayed physiological signals, said input interface also being operable to direct said control unit to identify a portion of the displayed annotating labels and a corresponding portion of said displayed physiological signals, said input interface being operable to direct said control means to display an alternate subset of annotating labels relating to such identified portion of annotating labels.

30. A programmer as defined in claim 27, further comprising means for synchronizing said current state signal, said first physiological signal and said second physiological signal.

31. A programmer as defined in claim 14, wherein said control means generates said current state signal by simulating said implantable medical device as a state machine using said vectors.

32. A programmer as defined in claim 14, wherein the subsets of annotating labels comprise:

(a) a subset consisting of traditional event markers;

(b) a subset consisting of traditional event markers supplemented with additional annotating labels; and (c) a subset comprising labels corresponding to each transition in the state of the implanted medical device.

33. A method, utilizing a programmer, for controlling the display of annotating labels relating to the operation of an implantable medical device, comprising the steps of:

receiving state vectors representing the current state of the implantable medical device;

generating a current state signal representative of the current state of the implantable medical device using the received state vectors;

storing in a memory means having a plurality of memory locations the current state signal in a first memory location;

generating annotating labels corresponding to the current state signal;

receiving a user input for selecting a subset of annotating labels to be displayed;

selecting a set of annotating labels to be displayed; and displaying said selected annotating labels.

34. The method defined in claim 33, wherein the step of displaying said selected annotating labels further comprises continuously updating the displayed annotating labels such that only the most recent annotating labels are displayed.

35. The method defined in claim 34, further comprising the steps of:

halting the updating of the displayed annotating labels;

identifying a portion of the displayed annotating labels; and displaying an alternate set of annotating labels relating to such identified portion of annotating labels.

36. The method defined in claim 35, wherein said alternate set is a superset of the prior displayed labels.

37. The method defined in claim 35, wherein said alternate set is a subset of the prior displayed annotating labels.

38. The method defined in claim 33, wherein said vectors are state transition vectors representing changes in the state of the implantable medical device.

39. The method defined in claim 33, wherein said vectors are current state vectors representing the current state of the implantable medical device.

40. The method defined in claim 33, wherein said vectors are current state vectors representing the current state of the implantable medical device and state transition vectors representing changes in the state of the implantable medical device.

41. The method defined in claim 33, wherein said vectors are also representative of concurrently detected events, further comprising the steps of:

generating a detected event signal from the received vectors;

storing the detected event signal; and generating annotating labels corresponding to said detected event signal.

42. The method defined in claim 33, wherein said implantable medical device also has means for detecting a physiological parameter and means for transmitting a physiological signal representative of the physiological parameter, further comprising the steps of:

receiving the physiological signal;

displaying the physiological signal; and storing the physiological signal in a second memory location.

43. The method defined in claim 33, further comprising the steps of:

detecting a first physiological parameter;

generating a first physiological signal from said detected first physiological parameter;

displaying said first physiological signal; and storing said first physiological signal in a second memory location.

44. The method defined in claim 43, further comprising the steps of:

updating the displayed annotating labels such that only the most recent annotating labels are displayed; and updating the displayed first physiological signal such that only the most recent first physiological signal is displayed.

45. The method defined in claim 44, further comprising the steps of:

halting the updating of the displayed annotating labels;

halting the updating of the displayed first physiological signal;

identifying a portion of the displayed annotating labels; and displaying an alternate subset of annotating labels relating to such identified portion of annotating labels.

46. The method defined in claim 43, wherein said implantable medical device also has means for detecting a second physiological parameter and means for transmitting a second physiological signal representative of the second physiological parameter, further comprising the steps of:

receiving the second physiological signal;

displaying the second physiological signal; and storing the second physiological signal in a third memory location.

47. The method defined in claim 46, further comprising the steps of:

updating the displayed annotating labels such that only the most recent annotating labels are displayed;

updating the displayed first physiological signal such that only the most recent first physiological signal is displayed; and updating the displayed second physiological signal such that only the most recent second physiological signal is displayed.

48. The method defined in claim 47, further comprising the steps of:

halting the updating of the displayed annotating labels;

halting the updating of the displayed first physiological signal;

halting the updating of the displayed second physiological signal;

identifying a portion of the displayed annotating labels; and displaying an alternate subset of annotating labels relating to such identified portion of annotating labels.

49. The method defined in claim 43, further comprising the step of synchronizing the current state signal and the first physiological signal.

50. The method defined in claim 46, further comprising the step of synchronizing the current state signal, the first physiological signal, and the second physiological signal.

51. The method defined in claim 42, further comprising the step of synchronizing the current state signal and the physiological signal.

52. The method defined in claim 33, wherein said step for generating a current state signal comprises generating a current state signal by simulating the implantable medical device as a state machine using said vectors.

53. The method defined in claim 33, wherein said implantable medical device is also a cardiac monitoring device.

54. The method defined in claim 33, wherein said implantable medical device is also a cardiac stimulating device.

55. The method defined in claim 46, wherein said implantable medical device is also a cardiac monitoring device, said first physiological signal is an electrocardiogram signal, and said second signal is an intracardiac electrogram signal.

56. The method defined in claim 33, where the subsets of annotating labels that can be selected comprise at least:
   (a) a subset consisting of traditional event markers;
   (b) a subset consisting of traditional event markers supplemented with additional annotating labels; and
   (c) a subset comprising labels corresponding to each transition in the state of the implanted medical device.

57. An apparatus for monitoring a parameter indicative of a patient's condition, comprising an implantable medical device having a plurality of operating states and an external monitoring device, wherein the implantable medical device comprises:
   means for detecting at least one physiological parameter of the patient and for producing a characteristic signal in response thereto;
   control means for comparing the characteristic signal to preset criteria for detecting the occurrence of a physiological event and for changing the operating state of said implantable medical device in response thereto;
   means for transmitting event codes representative of the state of the implantable medical device; and
   means for transmitting event codes representative of the occurrence of a physiological event;
   and wherein said monitoring device comprises:
      means for receiving said transmitted event codes;
      means for selectively displaying annotating labels, at least some of said annotating labels functioning to represent one or more of said received event codes;
      means for selectively determining annotating labels to be displayed; and
      means for simulating the implantable medical device as a state machine using said received event codes and for generating current state signals that are representative of the current state of said implantable medical device.

58. An apparatus, as defined in claim 57, wherein said means for detecting a physiological parameter comprises means for detecting a cardiac waveform.

59. An apparatus, as defined in claim 58, wherein said implantable medical device further comprises means for electrically stimulating the patient's heart.

60. An apparatus, as defined in claim 58, wherein said implantable medical device further comprises:
   means for transmitting said detected cardiac waveform;
   and wherein said monitoring device further comprises:
      means for receiving said transmitted cardiac waveform; and
      means for displaying said received cardiac waveform concurrently with said annotating labels as said cardiac waveform is received.

61. An apparatus, as defined in claim 60, further comprising:
   an input interface for directing said monitoring device to freeze a display for review thereon, whereby said input interface further comprises:
      means for highlighting a portion of the displayed cardiac waveform, and
      means for directing said monitoring device to display additional annotating labels to further explain the operation of said implantable medical device in the vicinity of said highlighted portion of said displayed cardiac waveform.

62. An apparatus, as defined in claim 60, wherein said monitoring device further comprises:
   means for receiving an electrocardiogram generated by an electrocardiogram measurement system; and
   means for displaying said received electrocardiogram concurrently with said received cardiac waveform and said annotating labels as said electrocardiogram is received.

63. An apparatus, as defined in claim 58, wherein said means for detecting said cardiac waveform comprises means for detecting the intracardiac electrogram, and wherein said implantable medical device transmits the patient's intracardiac electrogram to said monitoring device.

64. An apparatus, as defined in claim 57, wherein said means for transmitting event codes representative of the state of the implantable medical device comprises means for transmitting current state vectors, said current state vectors representing the current state of said implanted medical device.

65. An apparatus, as defined in claim 57, wherein said means for transmitting event codes representative of the state of the implantable medical device comprises means for transmitting state transition vectors, each state transition vector representing the change in state of said implantable medical device from the previous state transition vector.

66. An apparatus, as defined in claim 65, wherein said means for transmitting event codes representative of the state of the implantable medical device further comprises means for periodically transmitting current state vectors, said current state vectors representing the current state of said implanted medical device.

67. A programmer for use with an implantable medical device having means for transmitting vectors representative of the state of the implantable medical device, the programmer comprising:
   receiver means for receiving the transmitted vectors;
   memory means having a plurality of memory locations;
   control means for:
      (a) generating a current state signal from the received vectors by simulating said implantable medical device as a state machine using said vectors, such current state signal representative of the current state of the implantable medical device;
      (b) storing said current state signal in a first memory location; and
      (c) generating annotating labels corresponding to said current state signal; and
   means for displaying a selected subset of the annotating labels.

68. A programmer as defined in claim 67, wherein said vectors are state transition vectors representing changes in the state of the implantable medical device, and wherein said control means for generating a current state signal comprises means for generating a current state signal from state transition vectors.

69. A programmer as defined in claim 67, wherein said vectors are current state vectors representing the current state of the implantable medical device, and wherein said control means for generating a current state signal comprises means for generating a current state signal from current state vectors.

70. The programmer as defined in claim 67, wherein said vectors are current state vectors representing the current state of the implantable medical device and state transition vectors representing changes in the state of the implantable medical device, and wherein said control means for generating a current state signal comprises means for generating a current state signal from current state vectors and state transition vectors.

71. A programmer as defined in claim 67, wherein said vectors are also representative of concurrently detected events, wherein said control means further comprises:
   means for generating a detected event signal from the received vectors;
   means for storing said detected event signal; and
   means for generating annotating labels corresponding to said detected event signal.

72. A programmer as defined in claim 67, wherein said implantable medical device also has means for detecting a physiological parameter and means for transmitting a physiological signal representative of the physiological parameter, further comprising:
   means for receiving the physiological signal;
   means for displaying said physiological signal; and
   wherein said control means further comprises means for storing said physiological signal in a second memory location.

73. A method, utilizing a programmer, for controlling the display of annotating labels relating to the operation of an implantable medical device, comprising the steps of:
   receiving state vectors representing the current state of the implantable medical device;
   generating a current state signal representative of the current state of the implantable medical device using the received state vectors by simulating the implantable medical device as a state machine using said vectors;
   storing in a memory means having a plurality of memory locations the current state signal in a first memory location;
   generating annotating labels corresponding to the current state signal;
   selecting a set of annotating labels to be displayed; and
   displaying said selected annotating labels.

74. The method defined in claim 73, wherein said vectors are state transition vectors representing changes in the state of the implantable medical device.

75. The method defined in claim 73, wherein said vectors are current state vectors representing the current state of the implantable medical device.

76. The method defined in claim 73, wherein said vectors are current state vectors representing the current state of the implantable medical device and state transition vectors representing changes in the state of the implantable medical device.

77. The method defined in claim 73, wherein said vectors are also representative of concurrently detected events, further comprising the steps of:
   generating a detected event signal from the received vectors;
   storing the detected event signal; and
   generating annotating labels corresponding to said detected event signal.

78. The method defined in claim 73, wherein said implantable medical device is also a cardiac monitoring device.

79. The method defined in claim 73, wherein said implantable medical device is also a cardiac stimulating device.

80. An apparatus for monitoring a parameter indicative of a patient's condition, comprising an implantable medical device having a plurality of operating states and an external monitoring device, wherein the implantable medical device comprises:
   means for detecting at least one physiological parameter of the patient and for producing a characteristic signal in response thereto, wherein said means for detecting comprises means for detecting a cardiac waveform;
   control means for comparing the characteristic signal to preset criteria for detecting the occurrence of a physiological event and for changing the operating state of said implantable medical device in response thereto;
   means for transmitting event codes representative of the state of the implantable medical device; and
   means for transmitting event codes representative of the occurrence of a physiological event;
   and wherein said monitoring device comprises:
      means for receiving said transmitted event codes;
      means for selectively displaying annotating labels, at least some of said annotating labels functioning to represent one or more of said received event codes;
      means for selectively determining annotating labels to be displayed; and
   wherein said monitoring unit displays said annotating labels at one of three selected levels comprising:
      (a) a first level in which only annotating labels which comprise traditional event markers are displayed;
      (b) a second level in which said traditional event markers are supplemented with additional annotating labels; and
      (c) a third level in which an annotating label corresponding to each transition in the operating state of said implantable medical device is displayed on said monitor.

81. A method, utilizing a programmer, for controlling the display of annotating labels relating to the operation of an implantable medical device, comprising the steps of:
   receiving state vectors representing the current state of the implantable medical device;
   generating a current state signal representative of the current state of the implantable medical device using the received state vectors;
   storing in a memory means having a plurality of memory locations the current state signal in a first memory location;
   generating annotating labels corresponding to the current state signal;
   selecting a set of annotating labels to be displayed;
   displaying said selected annotating labels by continuously updating the displayed annotating labels such that only the most recent annotating labels are displayed;
   halting the updating of the displayed annotating labels;
   identifying a portion of the displayed annotating labels; and
   displaying an alternate set of annotating labels relating to such identified portion of annotating labels.

82. The method defined in claim 81, wherein said alternate set is a superset of the prior displayed labels.

83. The method defined in claim 81, wherein said alternate set is a subset of the prior displayed annotating labels.

* * * * *